United States Patent
Ali et al.

(10) Patent No.: US 12,128,019 B1
(45) Date of Patent: *Oct. 29, 2024

(54) NANOCOMPOSITE INCLUDING ABSCISIC ACID-LOADED COLLAGEN NANOPARTICLES

(71) Applicant: KING FAISAL UNIVERSITY, Al-Ahsa (SA)

(72) Inventors: Mai Mostafa Khalaf Ali, Al-Ahsa (SA); Hany Mohamed Abd El-Lateef Ahmed, Al-Ahsa (SA); Ahmed Mohammed Abu-Dief Mohammed, Al-Ahsa (SA); Hazem Mohamed Shaheen, Al-Ahsa (SA); Gaber Elsaber Abd El-Wanis Batiha, Al-Ahsa (SA); Manal Aly Shalaby, Al-Ahsa (SA); Rasha Mansour Nagi, Al-Ahsa (SA)

(73) Assignee: KING FAISAL UNIVERSITY, Al-Ahsa (SA)

( * ) Notice: Subject to any disclaimer, the term of this patent is extended or adjusted under 35 U.S.C. 154(b) by 0 days.

This patent is subject to a terminal disclaimer.

(21) Appl. No.: 18/210,250

(22) Filed: Jun. 15, 2023

(51) Int. Cl.
*A61K 31/19* (2006.01)
*A61K 9/16* (2006.01)
*A61P 9/10* (2006.01)

(52) U.S. Cl.
CPC ............ *A61K 31/19* (2013.01); *A61K 9/1658* (2013.01); *A61P 9/10* (2018.01)

(58) Field of Classification Search
None
See application file for complete search history.

(56) References Cited

U.S. PATENT DOCUMENTS

| | | | | |
|---|---|---|---|---|
| 6,303,150 | B1 * | 10/2001 | Perrier | B01J 13/14 264/4.1 |
| 2011/0054033 | A1 * | 3/2011 | Bassaganya-Riera | A61K 31/192 514/570 |
| 2021/0283055 | A1 | 9/2021 | Niyikiza et al. | |
| 2022/0227839 | A1 * | 7/2022 | Boz | A23J 1/10 |

FOREIGN PATENT DOCUMENTS

| | | | |
|---|---|---|---|
| EP | 2409710 | A1 | 1/2012 |
| WO | 2015012682 | A2 | 1/2015 |
| WO | WO-2021207566 | A1 * | 10/2021 |

OTHER PUBLICATIONS

Anwar et al. Theophylline-encapsulated Nile Tilapia fish scale-based collagen nanoparticles effectively target the lungs of male Sprague-Dawley rats. Scientific Reports. 12:4871; Published: Mar. 22, 2022 (Year: 2022).*
Wu et al. Collagen biomaterial for the treatment of myocardial infarction: an update on cardiac tissue engineering and myocardial regeneration. Drug Delivery and Translational Research. 9: 920-934; Published: Mar. 14, 2019 (Year: 2019).*
Elhadidy et al. Effect of Abscisic Acid on Isoproterenol-Induced Myocardial Infarction in Rats: A Possible Role of Nitric Oxide. Bulletin of Egyptian Society for Physiological Sciences. 40(2): 16-30; Published: Jul. 1, 2020 (Year: 2020).*
McLaughlin et al. Injectable human recombinant collagen matrices limit adverse remodeling and improve cardiac function after myocardial infarction. Nature Communications. 10: 4866; Published: Oct. 25, 2019 (Year: 2019).*
Dai et al. Delivering stem cells to the heart in a collagen matrix reduces relocation of cells to other organs as assessed by nanoparticle technology. Regenerative Medicine. 4(3): 387-395; Published: May 13, 2009 (Year: 2009).*
Nebulizer Breathing Treatments at Home: Patient Education. American Thoracic Society. Am J Respir Crit Care Med vol. 202, p. 7-p. 8, 2020 (Year: 2020).*
Shoulders and Raines. Collagen Structure and Stability. Annual Review of Biochemistry. 78: 929-958; Published: Apr. 3, 2009 (Year: 2009).*
Egorikhina et al. Changes in the Molecular Characteristics of Bovine and Marine Collagen in the Presence of Proteolytic Enzymes as a Stage Used in Scaffold Formation. Marine Drugs. 19(9): 502; Published: Sep. 2, 2021 (Year: 2021).*
Lu et al. Characterization and biological properties of marine by-product collagen through ultrasound-assisted extraction. Aquaculture Reports. 29: 101514; Published: Feb. 27, 2023 (Year: 2023).*
Sindhu, R.K. et al., "Bioactive Compounds and Nanodelivery Perspectives for Treatment of Cardiovascular Diseases," Appl. Sci. 11(22):11031 2021.

* cited by examiner

*Primary Examiner* — Juliet C Switzer
*Assistant Examiner* — Katherine Ann Holtzman
(74) *Attorney, Agent, or Firm* — Nath, Goldberg & Meyer; Joshua B. Goldberg

(57) ABSTRACT

A nanocomposite comprising collagen nanoparticles loaded with abscisic acid (ABA). can have an average particle diameter ranging from about 125 nm to about 185 nm. Collagen in the collagen nanoparticles can be derived from a marine source. The nanocomposite can effectively treat and prevent cardiac ischemia.

9 Claims, 5 Drawing Sheets

NANOCOMPOSITE INCLUDING ABSCISIC ACID-LOADED COLLAGEN NANOPARTICLES

BACKGROUND

1. Field

The disclosure of the present patent application relates to drug-loaded collagen nanoparticles, and particularly, to abscisic acid-loaded collagen nanoparticles for treating and preventing cardiac ischemia.

2. Description of the Related Art

A heart attack is usually caused by blockage of an artery. The heart muscle beyond the block is then deprived of oxygen and essential nutrients. This ischemia (literally "lack of blood flow") leads to many damaging changes, including calcium buildup in cells, high levels of reactive oxygen species ("ROS"), buildup of waste products such as lactic acid, and general energy depletion. These events may lead to cell death either by necrosis (i.e., directly from injury to the cells) or by apoptosis (i.e., from an energy dependent cell suicide process) and the formation of an infarct—a region of dead tissue. This process may be partially blocked by appropriate therapy.

Many prior treatments for ischemia have demonstrated adverse effects instead of benefits.

Thus, abscisic acid-loaded collagen nanoparticles solving the aforementioned problems are desired.

SUMMARY

The present subject matter relates to a nanocomposite comprising collagen nanoparticles loaded with abscisic acid (ABA). In an embodiment, the collagen nanoparticles have an average particle diameter ranging from about 125 nm to about 185 nm. In an embodiment, the collagen nanoparticles have an average particle diameter ranging from about 135 nm to about 175 nm. In an embodiment, collagen in the collagen nanoparticles is derived from a marine source. The nanocomposite can effectively treat and prevent cardiac ischemia.

In an embodiment, the present subject matter relates to a pharmaceutical composition including a nanocomposite and a pharmaceutically acceptable carrier, the nanocomposite including collagen nanoparticles loaded with abscisic acid. A method of treating and preventing cardiac ischemia in a subject can include administering to a subject in need thereof a therapeutically effective amount of the pharmaceutical composition.

These and other features of the present subject matter will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1A:
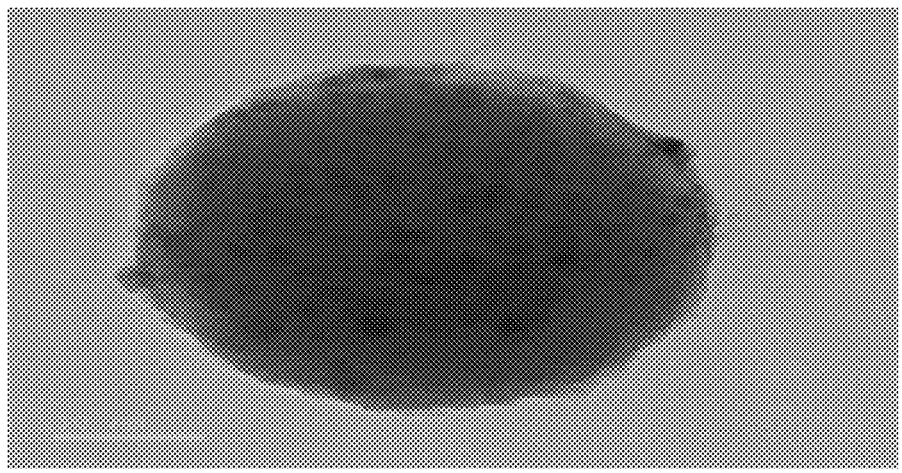
FIGS. 1A-1D are transmission electron microscopy (TEM) images of (A) abscisic acid (ABA) nanoparticles (B) (C), marine-collagen nanoparticles loaded with ABS (B,C), and (D) show loading of marine-collagen nanoparticles with ABS.
Figure 1B:
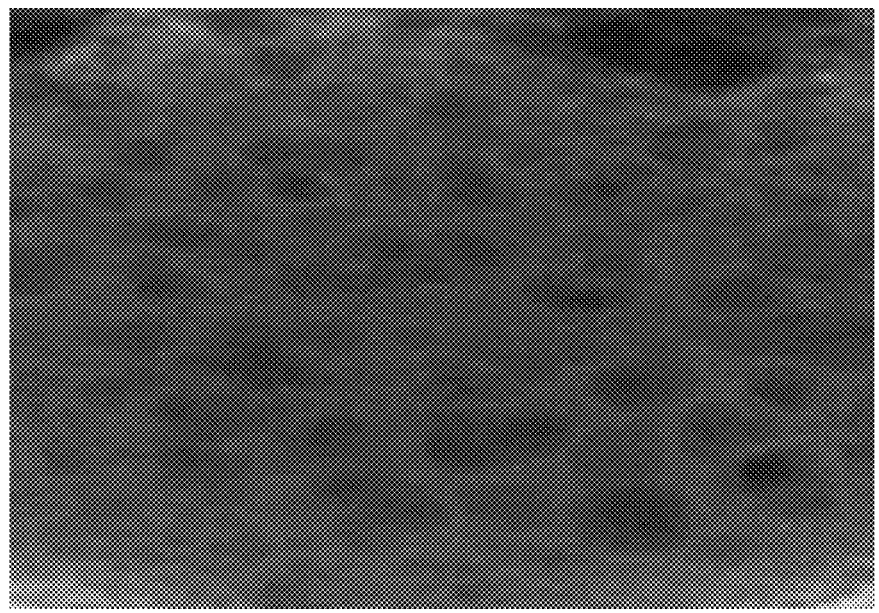

The following definitions are provided for the purpose of understanding the present subject matter and for construing the appended patent claims.

Definitions

It should be understood that the drawings described above or below are for illustration purposes only. The drawings are not necessarily to scale, with emphasis generally being placed upon illustrating the principles of the present teachings. The drawings are not intended to limit the scope of the present teachings in any way.

Throughout the application, where compositions are described as having, including, or comprising specific components, or where processes are described as having, including, or comprising specific process steps, it is contemplated that compositions of the present teachings can also consist essentially of, or consist of, the recited components, and that the processes of the present teachings can also consist essentially of, or consist of, the recited process steps.

It is noted that, as used in this specification and the appended claims, the singular forms "a", "an", and "the" include plural references unless the context clearly dictates otherwise.

In the application, where an element or component is said to be included in and/or selected from a list of recited elements or components, it should be understood that the element or component can be any one of the recited elements or components, or the element or component can be selected from a group consisting of two or more of the recited elements or components. Further, it should be understood that elements and/or features of a composition or a method described herein can be combined in a variety of ways without departing from the spirit and scope of the present teachings, whether explicit or implicit herein.

The use of the terms "include," "includes", "including," "have," "has," or "having" should be generally understood as open-ended and non-limiting unless specifically stated otherwise.

A "subject" herein is typically a human. In certain embodiments, a subject is a non-human mammal. Exemplary non-human mammals include laboratory, domestic, pet, sport, and stock animals, e.g., mice, cats, dogs, horses, and cows. As used herein, the term "patient" refers to any single subject for which treatment is desired. In certain embodiments, the patient herein is a human. A subject can be considered to be in need of treatment.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10% variation from the nominal value unless otherwise indicated or inferred.

Unless defined otherwise, all technical and scientific terms used herein have the same meaning as commonly understood to one of ordinary skill in the art to which the presently described subject matter pertains.

Where a range of values is provided, for example, concentration ranges, percentage ranges, or ratio ranges, it is understood that each intervening value, to the tenth of the unit of the lower limit, unless the context clearly dictates otherwise, between the upper and lower limit of that range and any other stated or intervening value in that stated range, is encompassed within the described subject matter. The upper and lower limits of these smaller ranges may independently be included in the smaller ranges, and such embodiments are also encompassed within the described subject matter, subject to any specifically excluded limit in the stated range. Where the stated range includes one or both of the limits, ranges excluding either or both of those included limits are also included in the described subject matter.

Throughout the application, descriptions of various embodiments use "comprising" language. However, it will be understood by one of skill in the art, that in some specific instances, an embodiment can alternatively be described using the language "consisting essentially of" or "consisting of".

In an embodiment, the present subject matter relates to a nanocomposite, comprising collagen nanoparticles loaded with abscisic acid (ABA). In an embodiment, the nanoparticles are generally spherical and can have an average particle diameter ranging from about 125 nm to about 185. The collagen nanoparticles can be derived from a marine source, such as mullet fish. As described herein, the nanocomposite can effectively treat and prevent cardiac ischemia. In an embodiment, the nanocomposite is administered orally.

ABA is a plant hormone but can also be found in fungi and mammals. In plants, ABA has a role in many plant development processes, such as plant ripening. Recently, ABA has demonstrated effectiveness in human disease treatment.

As described herein, encapsulation of ABA into collagen nanoparticles or the nanocomposite formulation can improve the therapeutic efficacy of ABA by enhancing its bioavailability. As set forth herein, when the nanocomposite was tested in vivo, all blood parameters confirmed the effectiveness of the nanocomposite for cardiac ischemia treatment.

In an embodiment, the nanocomposite can be administered in conjunction with a conventional drug for treating heart-related conditions. In an embodiment, the conventional drug can be Trimetazidine.

According to an embodiment, a method of synthesizing the nanocomposite can include combining equal parts abscisic acid and collagen nanoparticles in an aqueous solution to provide a mixture; and adding glutaraldehyde to the mixture to provide the nanocomposite.

In an embodiment, the nanocomposite can have an average particle size ranging from about 125 nm to about 185 nm. In other embodiments, the nanocomposite can have an average particle size ranging from about 135 nm to about 175 nm. In an embodiment, the nanoparticles have an average particle diameter of about 137 nm, about 170 nm, and/or about 173 nm.

An embodiment of the present subject matter is directed to a pharmaceutical composition comprising the nanocomposite and a pharmaceutically acceptable carrier.

An embodiment of the present subject matter is directed to a method of making a pharmaceutical composition including mixing the nanocomposite with a pharmaceutically acceptable carrier. For example, the method of making a pharmaceutical composition can include mixing the nanocomposite under sterile conditions with a pharmaceutically acceptable carrier with preservatives, buffers, and/or propellants to create the pharmaceutical composition.

To prepare the pharmaceutical composition, the nanocomposite, as the active ingredient, is intimately admixed with a pharmaceutically acceptable carrier according to conventional pharmaceutical compounding techniques. Carriers are inert pharmaceutical excipients, including, but not limited to, binders, suspending agents, lubricants, flavorings, sweeteners, preservatives, dyes, and coatings. In preparing compositions in oral dosage form, any of the pharmaceutical carriers known in the art may be employed. For example, for liquid oral preparations, suitable carriers and additives include water, glycols, oils, alcohols, flavoring agents, preservatives, coloring agents, and the like. Further, for solid oral preparations, suitable carriers and additives include starches, sugars, diluents, granulating agents, lubricants, binders, disintegrating agents, and the like.

The present compositions can be in unit dosage forms such as tablets, pills, capsules, powders, granules, ointments, sterile parenteral solutions or suspensions, metered aerosol or liquid sprays, drops, ampules, auto-injector devices or suppositories, for oral parenteral, intranasal, sublingual or rectal administration, or for administration by injection, inhalation or insufflation. The nanocomposite can be mixed under sterile conditions with a pharmaceutically acceptable carrier and, if required, any needed preservatives, buffers, or propellants. The composition can be presented in a form suitable for daily, weekly, or monthly administration. The pharmaceutical compositions herein will contain, per dosage unit, e.g., tablet, capsule, powder, injection, teaspoonful, suppository and the like, an amount of the active ingredient necessary to deliver an effective dose. A therapeutically effective amount of the nanocomposite or an amount effective to treat a disease, such as cardiac ischemia, may be determined initially from the Examples described herein and adjusted for specific targeted diseases using routine methods.

The nanocomposite can be administered to a subject in need thereof. In an embodiment, the nanocomposite can be administered to a subject in need thereof to treat cardiac ischemia.

An embodiment of the present subject matter is directed to a method of treating and preventing cardiac ischemia in a subject, comprising administering to a subject in need thereof a therapeutically effective amount of the pharmaceutical composition according to the present subject matter. In an embodiment, a therapeutically effective amount of the pharmaceutical composition can be 1 mg/kg/day.

The nanocomposite or pharmaceutical compositions thereof can be administered to a subject by any suitable route. For example, the compositions can be administered orally (including bucally and sublingually), nasally, rectally, intracisternally, intra vaginally, intraperitoneally, topically, transdermally (as by powders, ointments, or drops), and/or parenterally. As used herein, "parenteral" administration refers to modes of administration other than through the gastrointestinal tract, which include intravenous, intramuscular, intraperitoneal, intrasternal, intramammary, intraocular, retrobulbar, intrapulmonary, intrathecal, subcutaneous and intraarticular injection and infusion. Surgical implantation may also be contemplated, including, for example, embedding a composition of the disclosure in the body such as, for example, in a tissue, in the abdominal cavity, under the splenic capsule, brain, or in the cornea.

The present teachings are illustrated by the following examples.

Example 1

Synthesis of Collagen Nanoparticles

Scales of grey mullet fish were isolated by hand and cleaned with distilled water. The samples were dried, placed in polyethylene bags, and kept at 25° C. until use. Fish scales were treated with 0.1 N NaOH to remove non-collagenous proteins and pigments at a sample-to-alkali solution ratio of 1:8 (w/v) for 3 days, followed by washing with distilled water and drying. The samples were extracted with 0.5 M acetic acid at a sample-to-acid ratio of 1:2.5 (w/v) for three days followed by centrifugation at 10,000 rpm for 1 h at 4° C. The supernatants were pooled and salted out by adding NaCl at a final concentration of 0.9 M. The pellets were collected by centrifugation and washed three times with distilled water to remove any residual salts. Finally, the pellets were suspended in 0.5 M acetic acid and salts were removed using dialysis and then lyophilized.

Nanoprecipitation was used to create collagen nanoparticles using a non-solvent (ethanol). Ethanol 100 ml was added dropwise to 100 ml of 0.5 M acetic acid solution of collagen concentration of 1 w/v % using a burette with free-flow under stirring in order to dehydrate the collagen resulting in a conformational change from fibers to spheres conformation so that collagen nanoparticles with a milky appearance were obtained. After the desolvation process, glutaraldehyde was added to induce particle crosslinking.

Example 2

Preparation of Nanocomposite

ABA (10 mg) was added step-wise to an aqueous solution of 10 mg collagen nanoparticles (1 w/v %) with continuous stirring for 4 hours. Glutaraldehyde (500 μL) was added as a cross-linking material to form the collagen nanoparticles. The drug-encapsulated nanoparticle solution was centrifuged, lyophilized, and stored for further usage.

Example 3

In Vitro Cytotoxicity and Cell Viability

In vitro cell viability and cytotoxicity assays with cultured cells are widely used for cytotoxicity tests of chemicals and for drug screening. Application of these assays has been of increasing interest over recent years. Cell viability and cytotoxicity assays are based on various cell functions such as cell membrane permeability, enzyme activity, cell adherence, ATP production, co-enzyme production, and nucleotide uptake activity.

On the NHSF cell line, the cytotoxic effect of ABA alone and collagen nanoparticles loaded with ABA was investigated with serial double-fold dilutions at an initial dose of 50 μMABA. ABA loaded with collagen nanoparticles was dissolved in ethanol, 0.0264 g/mL stock solutions, which were then serially diluted in a complete growth medium to make the different concentrations used in cytotoxicity assays. The cytotoxicity of each drug against the NHSF cell line was determined using an optical microscope. After a 24-hour incubation period at 37° C., exponentially developing cells were seeded in 96-well flat-bottomed microplates and subjected to drug doses for 48 hours.

After exposure of the NHSF cell line to each experimental drug, the reactions were allowed to proceed in an incubator (37° C./5% $CO_2$/95% humidity) for 24 hours and 72 hours of time. Cell viability was recorded through an optical microscope, which is one of the methods generally used to detect cell proliferation or toxicity.

After 24 hours, cell growth rates in different types of ABA and "Marine Collagen Nanoparticles (MCNPs) with ABA were observed under an optical microscope. Cells were also cultured in media containing ethanol in an incubator (37° C./5% $CO_2$/95% humidity) and then observed under an optical microscope. The cells exhibited normal morphology of branch- and spindle-shapes.

After 72 hours, the colonies exhibited representative human ESC-like morphology, which includes a large nucleoli and nucleus to cytoplasm ratio. The cells were packed tightly and borders were distinct, demonstrating an elongated, flat, and spindle-like morphology. The cells covered the majority of the surface area of the culture plate. HSFs culture demonstrated a marked increase of proliferation upon treatment with ABA. MCNPs loaded with ABA demonstrated higher cell proliferation.

Example 4

Physicochemical Characterization

Observation of the specimens was performed under a scanning electron microscope. Photomicrographs were performed under different magnifications ranging from ×15,000 to ×35,000 and voltage 20-30 kV. Scanning electron microscopy (SEM) was used to investigate ABA, MCNPs, MCNPs load ABA to determine their superficial morphology as well as their composition, crystallography and orientation. SEM was used to examine the microstructure of the fish collagen and its nano-formulations. The lyophilized collagen samples were cut using a punch and fixed to an adhesive carbon stub. Imaging was carried out using a Tabletop SEM (JEOL 6340, Japan) operated at 15 kV.

Images of MCNPs and MCNPs loaded with ABA revealed different sizes (0.14-0.43 μm) of spherical structures and fairly smooth surfaces in both. The SEM analysis revealed that the particles are distributed throughout the sample without cluster formation. SEM further revealed microstructure of freeze-dried natural ABA and MCNPs as well as homogeneous multi-layered aggregates, strict, ordered, and highly fibrillary structures.

Fourier-transform infrared (FTIR) is a tool for measuring the radiation absorption of infrared regions at various wavelengths. This test was used to identify ABA, MCNPs, and MCNPs loaded with ABA compounds. Samples were placed on a disk printer and then vacuumed to remove the gas content. The printed disk was then inserted into the FTIR tool and measured at a wavelength of 400 to 4,000 cm-1.

Figure 2A:
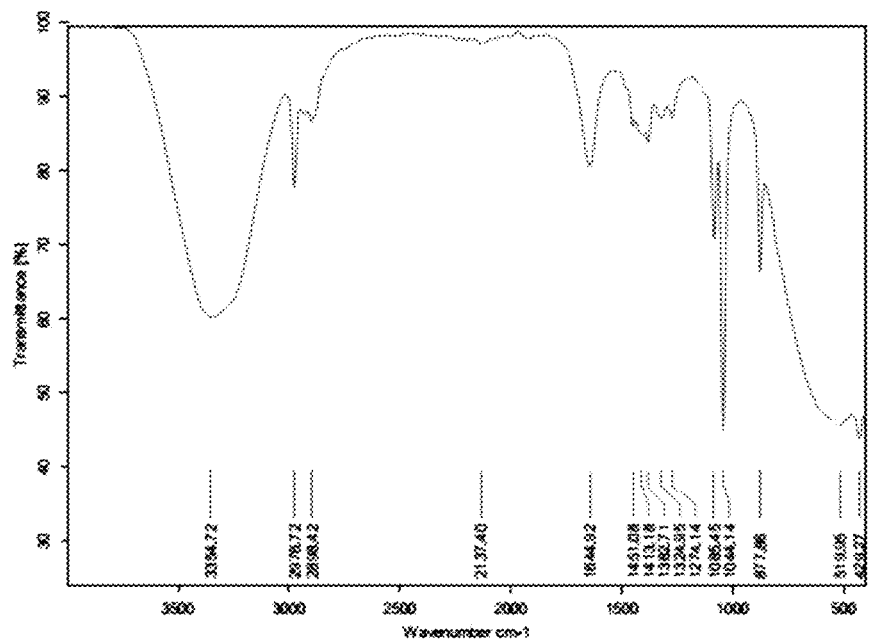
FIGS. 2A-2B are Fourier Transform Infrared Spectroscopy (FTIR) spectra for (A) standard marine collagen nanoparticles and (B) and the nanocomposite according to the present teachings.
Figure 2B:
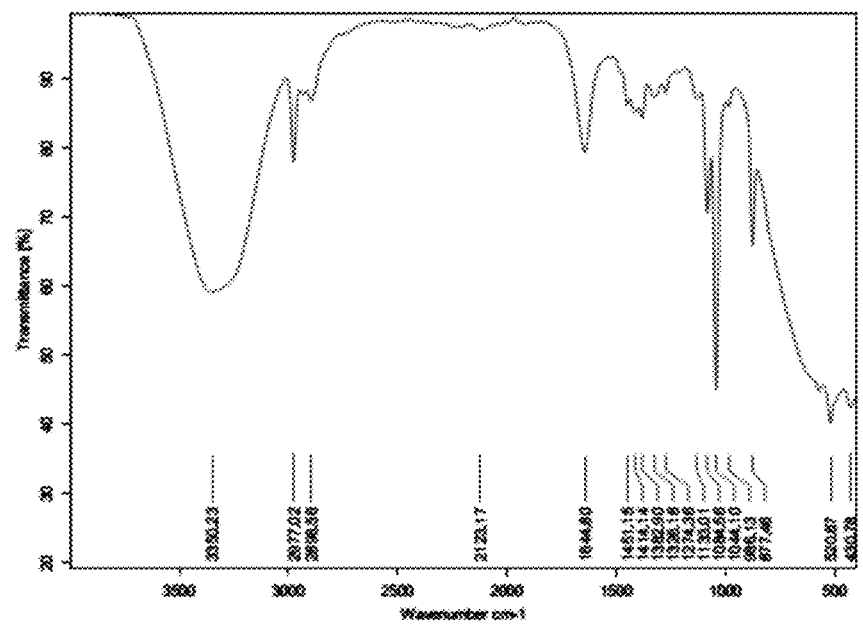
Figures 3A, 3B, 3C, 3D, 3E:
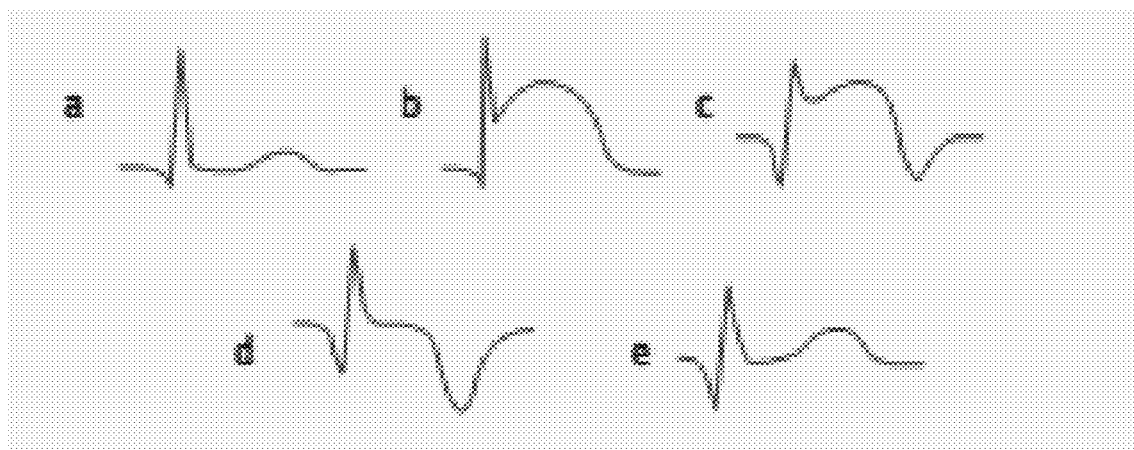
FIGS. 3A-3E show sequential changes of acute myocardial infarction on ECG for (3A) the control, negative group; (3B) the MI group; (3C) the MI+ABA group; (3D) the MI+Trimetazidine group; and (3E) the MI+collagen nanoparticle group.

The spectrum of the ABA collagen nanoparticle (FIGS. 2A-2B) showed bands for amide I at 1644.92 cm-1, amide II at 1451.08 cm-1, amide III at 1044.14 cm-1, amide A at 3354.72 cm-1, amide B at 2976.72 cm-1. The spectrum of the collagen nanoparticle showed bands for amide I at 1644.8 cm-1, amide II at 1451.15 cm-1, amide III at 1044.10 cm-1, amide A at 3350.23 cm-1, amide B at 2977.02 cm-1.

The nano formulations were morphologically examined using a technique called transmission electron microscopy (TEM) (TALOS Instrument, Thermo Fischer Scientific, United States) at SRTA-City, Egypt. The sample preparation involved the loading of a few drops of the nanoparticles on a carbon-coated copper grid and then negatively staining them using 1% phosphotungstic acid (PTA). The excess stain solution was removed using filter paper followed by air drying. The next step involved the examination of the stained films using a TEM instrument. The films on the TEM grids were allowed to dry prior to measurement. Serial-section TEM (system) is also used to determine the 3D organization of examined drugs.

Figure 1C:
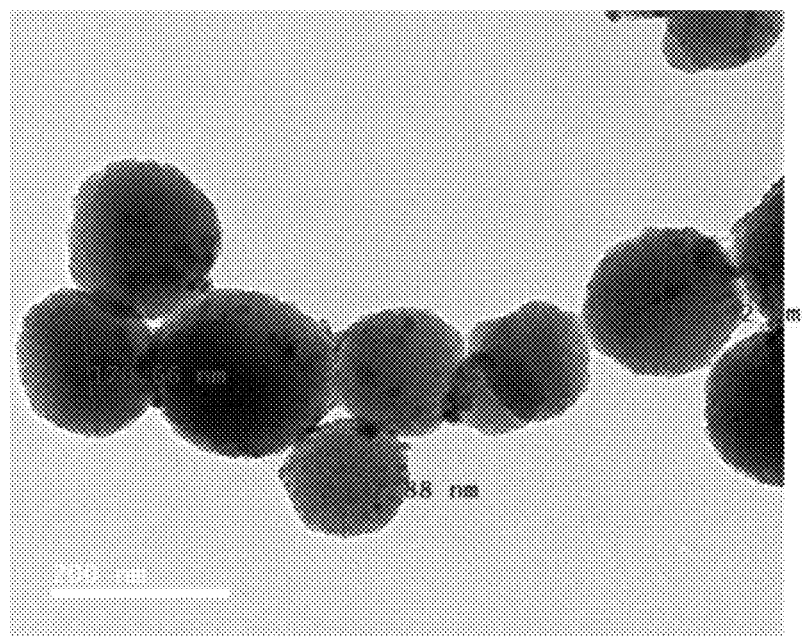
Figure 1D:
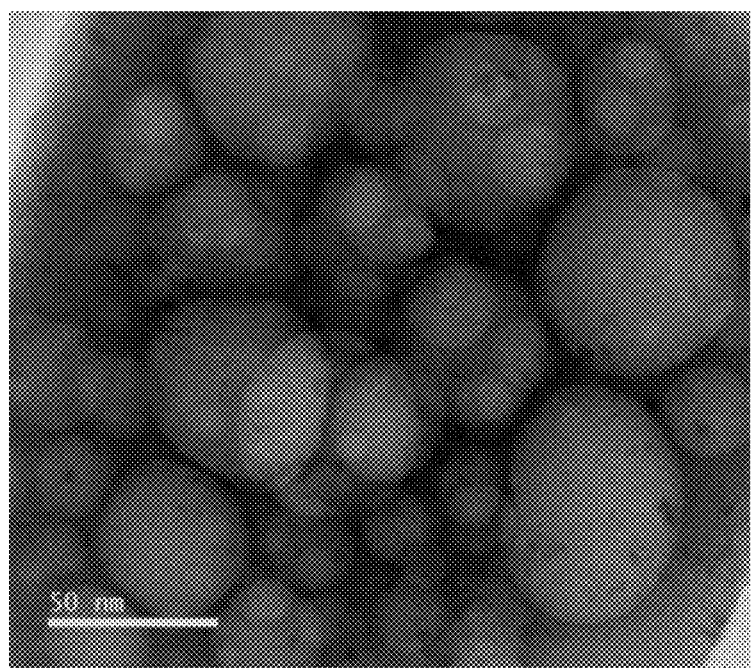

TEM images (FIGS. 1A-1D) show spherical collagen nanoparticles with a size of 137, 170, and 173 nm, where the surface of most of the fish scale-based collagen nanoparticles is decorated with a protein shell. FIGS. 1C and 1D show that MCNPs have an asymmetrical shape. FIG. 1A shows that ABA became very small in size, suggesting its conversion into nanoparticles during loading in the MCNPs.

Example 5

In Vivo Testing

Four groups of rats were injected with adrenaline (2 mg/kg, s.c.) as a single dose for 2 consecutive days (24 h apart) to induce myocardial infarction (MI) while an additional rat group was used as control. Treatment of the rat groups is set forth below.

Group 1: (Control negative group): rats were injected intraperitoneally (i.p.) with physiological saline 0.2 ml/day for one week.

Group 2 (MI group): rats were injected with adrenaline (2 mg/kg, s.c.) as a single dose for 2 consecutive days (24 h apart) to induce MI.

Group 3 (MI+ABA carrying on collagen nanoparticle): rats were injected with adrenaline (2 mg/kg, s.c.) as a single dose for 2 consecutive days (24 h apart) to induce MI and ABA-loaded collagen nanoparticle were administered with adrenaline by oral gavage for one week 1 mg/kg/day of.

Group 4 (MI+Trimetazidine): rats were injected with adrenaline (2 mg/kg, s.c.) as a single dose for 2 consecutive days (24 h apart) to induce MI and Trimetazidine (Sigma, USA) was administered intraperitoneally with adrenaline at 10 mg/kg/day for one week. Trimetazidine was injected intraperitoneally in the low-dose group (10 mg/kg).

Group 5 (MI+Collagen nanoparticle) group: rats were injected with adrenaline (2 mg/kg, s.c.) as a single dose for 2 consecutive days (24 h apart) to induce MI Collagen nanoparticle was administered along with adrenaline by oral gavage for one week at 1 mg/kg/day.

Group 6 (MI+ABA carrying on collagen nanoparticle+ Trimetazidine) group: rats were injected with adrenaline (2 mg/kg, s.c.) as a single dose for 2 consecutive days (24 h apart) to induce MI, and ABA-loaded collagen nanoparticle were administered (1 mg/kg/day) by oral gavage and 10 mg/kg/day with Trimetazidine administered intraperitoneally (i.p.) along with adrenaline for one week.

An ECG (FIGS. 3A-3E) of the normal control group showed a normal cardiograph, while rats in the Adrenaline-induced MI group, and rats in the collagen nanoparticle group showed pathological changes such as ST-segment elevation, and decreased RR interval. Standard and extracted rat groups still showed pathological changes but with the ST segment nearer to the isoelectric line. ABA-loaded collagen nanoparticles and commercial drug treated rats showed almost normal electrocardiogramith little to no elevation in the ST-segment. Combined treatment groups showed a normal ECG with no elevation of ST-segment and no shortening of R-R interval. The results are summarized in Table 1.

TABLE 1

| | Parameters of Electrocardiogram Assessments | | | | | |
|---|---|---|---|---|---|---|
| Group | carotid flow mean (ml/min) | HR (meanb/min) | COP (meanml/min) | Stroke volume (meanml/min) | ST height(mm) | RR (interval/sec) |
| 1. Control/normal | $23.72 \pm 0.04^a$ | $239 \pm 1.37^d$ | $23.82 \pm 0.0^a$ | $0.1 \pm 0.001^a$ | $21.25 \pm 0.43^d$ | $0.75 \pm 0.00^a$ |
| 2. MI | $10.65 \pm 0.04^c$ | $267 \pm 1.24^{ab}$ | $10.75 \pm 0.0^c$ | $0.04 \pm 0^c$ | $50.87 \pm 0.99^a$ | $0.67 \pm 0.00^d$ |
| 3. Standard ABA | $17.4 \pm 0.16^b$ | $255.77 \pm 1.23^c$ | $17.52 \pm 0.1^b$ | $0.069 \pm 0.001^b$ | $39.33 \pm 2.15^b$ | $0.7 \pm 0.003^c$ |
| 4. Extracted ABA | $18.06 \pm 1.15^b$ | $247.4 \pm 9.69^{cd}$ | $18.57 \pm 1.0^b$ | $0.077 \pm 0.009^b$ | $42.98 \pm 4.05^b$ | $0.73 \pm 0.03^b$ |
| 5. Collagen nano/ABA | $23.8 \pm 0.08^a$ | $257 \pm 1.41^{bc}$ | $24.16 \pm 0.1^a$ | $0.094 \pm 0.001^a$ | $26.64 \pm 0.69^c$ | $0.74 \pm 0.05^{ab}$ |
| 6. trimetazidine | $23.75 \pm 0.05^a$ | $254.17 \pm 1.89^c$ | $23.9 \pm 0.07^a$ | $0.094 \pm 0.001^c$ | $27.55 \pm 0.49^c$ | $0.75 \pm 0.02^a$ |
| 7. collagen nano | $10.68 \pm 0.04^c$ | $271.83 \pm 1.89^a$ | $10.73 \pm 0.0^c$ | $0.039 \pm 0^a$ | $51.86 \pm 0.7^a$ | $0.66 \pm 0.00^d$ |
| 8. combined | $23.83 \pm 0.06^a$ | $247.17 \pm 1.87^d$ | $23.82 \pm 0.0^a$ | $0.096 \pm 0.001^a$ | $22.1 \pm 0.4^a$ | $0.73 \pm 0.00^b$ |

Means with the same letter are not significantly different from each other (P < 0.05).

As shown in Table 1, there was a significant ST-segment elevation (by about 139%) after adrenaline injection compared to the control rats, which denotes a recent myocardial injury. In addition, there was also a significant decrease in RR interval (by about 10%) denoting an increase in heart rate induced probably by compensatory sympathetic stimulation.

Treatment with collagen nanoparticles shows almost the same results as the MI group with an elevation of the ST segment by about 144% and a decrease in RR interval by about 12%. ABA-loaded collagen nanoparticles, commercial drugs, as well the combined group show a significant decrease in the ST segment elevation compared to the MI group (by about 48%, 46%, 57% respectively) with almost no significant change compared to the normal control group especially in the combined group.

Overall, these changes demonstrate the therapeutic effect of abscisic acid-loaded collagen nanoparticles on MI and the enhanced effect of abscisic acid-loaded collagen nanoparticles when combined with a commercial drug, Trimetazidine. The untreated myocardial infarcted group demonstrated reduced carotid blood flow, stroke volume (SV), and cardiac output (COP) by about 55%, 60%, and 54%, respectively, greater than the normal controls.

When comparing rats treated with abscisic acid-loaded collagen nanoparticles and the MI group, the abscisic acid-loaded collagen nanoparticles significantly elevated carotid blood flow, SV, and COP by about 123%, 135%, and 125%, respectively. These effects were more pronounced when compared to the standard and extracted groups where carotid blood flow, SV, and COP were 63%, 73% and 63% in the standard group and 70%, 93% and 73% in the extracted group. The combination of abscisic acid with the commercial drug, showed the most significant improvement in the carotid blood flow, SV, and COP show in 124%, 125%, 122% increase compared to the MI group with no significant difference from the normal control group. This pattern of effectiveness was consistent with findings obtained regarding body weight and heart weight of the experimental rats (Table 2) as well as oxidative stress markers and antioxidant enzymes (Table 3).

TABLE 2

Body and heart weight of experimental rats

| Group | Bwt | Hwt |
| --- | --- | --- |
| 1. Control normal | 200 ± 3.54$^a$ | 1.2 ± 0.02$^e$ |
| 2. MI | 155.2 ± 1.77$^e$ | 1.74 ± 0.04$^a$ |
| 3. Collagen nano/ABA | 193 ± 2.55$^{abc}$ | 1.36 ± 0.03$^d$ |
| 4. Trimetazidine | 188 ± 1.22$^{bcd}$ | 1.39 ± 0.03$^{cd}$ |
| 5. Collagen nano | 187 ± 3.39$^{cd}$ | 1.59 ± 0.03$^b$ |
| 6. Combined | 194 ± 1.87$^{ab}$ | 1.34 ± 0.03$^d$ |

Means with the same letter are not significantly different from each other ($P < 0.05$).

TABLE 3

Analyses of oxidative stress markers and antioxidant enzymes

| Group | MDA (μmol/g protein) | NO (μM/g protein) | GSH (μmol/g protein) | Catalase (U/g protein) |
| --- | --- | --- | --- | --- |
| 1. Control normal | 3.2 ± 0.00$^e$ | 35 ± 0$^c$ | 19.3 ± 0$^a$ | 176 ± 0$^a$ |
| 2. MI | 11.13 ± 0.3$^a$ | 103.06 ± 3.05$^a$ | 14.29 ± 0.13$^b$ | 64 ± 0.58$^c$ |
| 3. Collagen nano/ABA | 7.5 ± 1.15$^b$ | 71.11 ± 15.72$^b$ | 18.25 ± 0.74$^{ab}$ | 126.5 ± 29.16$^{abc}$ |
| 4. Trimetazidine | 4.4 ± 0.26$^{cde}$ | 52.22 ± 0$^{bc}$ | 19.59 ± 2.28$^a$ | 132.5 ± 36.08$^{ab}$ |
| 5. Collagen nano | 3.65 ± 0.2$^{de}$ | 39.17 ± 1.76$^c$ | 20.43 ± 0.32$^a$ | 91.5 ± 1.44$^{bc}$ |
| 6. Combined | 4.63 ± 0.1$^{cde}$ | 66.94 ± 10.1$^b$ | 20.54 ± 1.67$^a$ | 92 ± 7.51$^{bc}$ |

Means with the same letter are not significantly different from each other ($P < 0.05$).

As shown in Table 3, adrenaline administration elevated MDA (marker of lipid peroxidation), reduced GSH (endogenous anti-oxidant), and decreased CAT cardiac contents in the experimental rats. All treatment drugs improved the marker levels. NO level increased due to adrenaline administration because the role of NO in cardiovascular diseases is complex and controversial.

As shown in Table 4, adrenaline administration elevated serum levels of cardiac enzymes; troponin, LDH, and CK levels in all groups which received adrenaline injection, and this reveals that adrenaline administration leads to myocardial damage and leakage of cardiac enzymes into the circulation. Cardiac enzyme levels decreased toward normal in ABA-loaded MCNPs, extracted ABA, combined drugs, and standard ABA-treated groups.

TABLE 4

Analyses of Biological Cardiac Markers

| Group | LDH (U/L) | CK-MB (U/L) | Troponin (ng/ml) |
| --- | --- | --- | --- |
| 1. Control normal | 442.00 ± 64.00$^c$ | 0.75 ± 0.05$^d$ | 1.05 ± 0.15$^e$ |
| 2. MI | 978.00 ± 22.00$^a$ | 1.46 ± 0.06$^a$ | 2.2 ± 0.1$^a$ |
| 3. Collagen nano/ABA | 412.67 ± 4.98$^c$ | 1.21 ± 0.02$^b$ | 1.78 ± 0.02$^b$ |
| 4. Trimetazidine | 246.67 ± 12.47$^d$ | 1.13 ± 0.02$^{bc}$ | 1.34 ± 0.03$^d$ |
| 5. Collagen nano | 284.33 ± 27.72$^d$ | 1.16 ± 0.02$^{bc}$ | 1.54 ± 0.04$^c$ |
| 6. Combined | 463.33 ± 82.61$^{bc}$ | 1.09 ± 0.04$^c$ | 1.75 ± 0.02$^b$ |

Means with the same letter are not significantly different from each other ($P < 0.05$).

It is to be understood that the nanocomposite including abscisic acid-loaded collagen nanoparticles is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A nanocomposite, consisting of:
   collagen nanoparticles loaded with abscisic acid (ABA) nanoparticles; and
   glutaraldehyde.

2. The nanocomposite of claim 1, wherein the collagen nanoparticles have an average particle diameter ranging from about 125 nm to about 185 nm.

3. The nanocomposite of claim 1, wherein the collagen nanoparticles have an average particle diameter ranging from about 135 nm to about 175 nm.

4. A method of treating and preventing cardiac ischemia in a subject, comprising administering to a subject in need thereof a therapeutically effective amount of the nanocomposite of claim 1.

5. A method of synthesizing the nanocomposite of claim 1, the method consisting of:
   combining equal parts abscisic acid and collagen nanoparticles in an aqueous solution to provide a mixture; and
   adding glutaraldehyde to the mixture to provide the nanocomposite of claim 1.

6. A pharmaceutical composition consisting of a nanocomposite and a pharmaceutically acceptable carrier, the nanocomposite consisting of:
   collagen nanoparticles loaded with abscisic acid nanoparticles; and
   glutaraldehyde.

7. A method of treating and preventing cardiac ischemia in a subject, comprising administering to a subject in need thereof a therapeutically effective amount of the pharmaceutical composition of claim 6.

8. The method of claim 7, wherein the collagen nanoparticles have an average particle diameter ranging from about 125 nm to about 185 nm.

9. The method of claim 7, wherein the collagen nanoparticles have an average particle diameter ranging from about 135 nm to about 175 nm.

* * * * *

UNITED STATES PATENT AND TRADEMARK OFFICE
CERTIFICATE OF CORRECTION

PATENT NO. : 12,128,019 B1
APPLICATION NO. : 18/210250
DATED : October 29, 2024
INVENTOR(S) : Ali et al.

It is certified that error appears in the above-identified patent and that said Letters Patent is hereby corrected as shown below:

On the Title Page

Item (72):
Please remove Inventor 3 residence "AL-AHSA (SA)" and replace with "Al-Madina Al-Mounawara (SA)".
Please remove Inventor 4 residence "AL-AHSA (SA)" and replace with "Damanhour (EG)".
Please remove Inventor 5 residence "AL-AHSA (SA)" and replace with "Damanhour (EG)".
Please remove Inventor 6 residence "AL-AHSA (SA)" and replace with "Alexandria (EG)".
Please remove Inventor 7 residence "AL-AHSA (SA)" and replace with "Damanhour (EG)".

Signed and Sealed this
Third Day of December, 2024

Katherine Kelly Vidal
*Director of the United States Patent and Trademark Office*